United States Patent [19]  
Hiestand

[11] 4,264,516  
[45] Apr. 28, 1981

[54] QUATERNARY AMMONIUM SALTS OF ANTISTATIC AGENTS OR SOFTENING AGENTS CONTAINING FATTY ACID RADICALS, PROCESS FOR THE PRODUCTION AND USE THEREOF

[75] Inventor: Armin Hiestand, Binningen, Switzerland

[73] Assignee: Ciba-Geigy Corporation, Ardsley, N.Y.

[21] Appl. No.: 925,062

[22] Filed: Jul. 17, 1978

[30] Foreign Application Priority Data

Aug. 1, 1977 [LU] Luxembourg ............................ 77887

[51] Int. Cl.³ ................................................ C11D 1/40
[52] U.S. Cl. ................................ 260/404.5 A; 252/8.8; 252/545; 252/547; 548/354
[58] Field of Search ........................... 260/403, 404.5 Q

[56] References Cited

U.S. PATENT DOCUMENTS

| | | | |
|---|---|---|---|
| 2,268,395 | 12/1941 | Henke et al. | 260/404.5 X |
| 2,286,794 | 6/1942 | Dickey et al. | 252/8.8 |
| 2,357,598 | 9/1944 | Mauersherger | 260/403 X |
| 2,523,934 | 9/1950 | Albrecht et al. | |
| 2,742,379 | 4/1956 | Schofield | |
| 2,785,092 | 3/1957 | Hiestand | |
| 2,836,517 | 5/1958 | Gruber et al. | 260/404.5 X |
| 3,060,185 | 10/1962 | Druey et al. | 260/404.5 X |
| 3,082,227 | 3/1963 | Sherr | 260/404.5 |
| 3,174,985 | 3/1965 | Berger | 260/404.5 |
| 3,211,646 | 10/1965 | Berger | 252/8.8 |
| 3,539,601 | 11/1970 | Lewis | 260/403 |
| 3,775,446 | 11/1973 | Wegerhoff et al. | 260/403 |
| 3,956,243 | 5/1976 | Loss et al. | |
| 3,984,335 | 10/1976 | Cike et al. | 252/8.8 |
| 4,110,263 | 8/1978 | Lindemann et al. | 252/545 |
| 4,181,634 | 1/1980 | Kennedy et al. | 252/545 |
| 4,215,064 | 7/1980 | Lindemann | 260/403 |

FOREIGN PATENT DOCUMENTS 45-28885 9/1970 Japan ........................................ 260/403
782974 9/1957 United Kingdom .

*Primary Examiner*—Ethel G. Love
*Attorney, Agent, or Firm*—Edward McC. Roberts; John P. Spitals

[57] ABSTRACT

The present invention relates to water-soluble quaternary ammonium salts of organic compounds having antistatic or softening properties. These ammonium salts contain at least one fatty acid radical and are quaternized with a dialkyl ester of an alkylphosphonic acid. They are used for finishing organic fibrous material, especially textiles and paper.

9 Claims, No Drawings

QUATERNARY AMMONIUM SALTS OF ANTISTATIC AGENTS OR SOFTENING AGENTS CONTAINING FATTY ACID RADICALS, PROCESS FOR THE PRODUCTION AND USE THEREOF

The invention relates to a water-soluble quaternary ammonium salt of an antistatic agent for softening agent that contains at least one fatty acit radical and is quaternised with a dialkyl ester of an alkylphosphonic acid containing identical alkyl radicals each having 1 or 2 carbon atoms.

Known antistatic agents or softening agents are quaternised for example with quaternising agents, such as methyl chloride or dimethyl sulphate, or they are in the form of ammonium salts of inorganic or organic acids, such as acetic acid or phosphoric acid. Organic fibrous material, for example textile fabric or paper, treated with these known antistatic agents or softening agents, exhibits a deleterious rust formation, i.e. rust spots, when it comes into contact with iron-containing objects, such as paper clips or nails.

Surprisingly, it has now been found that this deleterious rust formation can be substantially diminished if the tertiary amine salts of softening agents or antistatic agents, which are in themselves known, are quaternised with a dialkyl ester of an alkylphosphonic acid of the indicated kind.

Preferred ammonium salts of the present invention have the formula

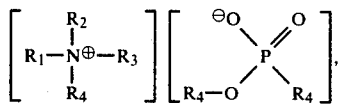  (1)

wherein $R_1$ represents a radical of one of the formulae $$A_1-CO-NH-(CH_2-O)_{x_1-1}-(CH_2)_{n_1}- \quad (1.1)$$

or

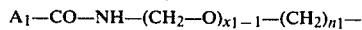  (1.2)

each of $R_2$ and $R_3$ represents a radical of the formula $$A_3-CO-NH-(CH_2-O)_{x_2-1}-(CH_2)_{n_3}-, \quad (1.3)$$

alkyl of 1 to 4 carbon atoms, cyanoalkyl of 2 or 3 carbon atoms or hydroxyalkyl of 2 or 3 carbon atoms which is free or etherified by alkyl of 1 to 4 carbon atoms, or $R_2$ and $R_3$ together with the quaternary nitrogen atom to which they are attached represent a ring of the formula

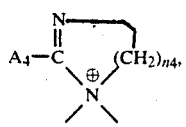  (1.4)

$R_4$ represents ethyl or preferably methyl, each of $A_1$, $A_2$, $A_3$ and $A_4$ represents alkyl or alkenyl of 9 to 21 carbon atoms, each of $x_1$ and $x_2$ is 1 or 2, and each of $n_1$, $n_2$, $n_3$ and $n_4$ is 2 or 3.

The radicals $A_1$ to $A_4$ in the formulae (1.1) to (1.4) are derived from saturated or unsaturated fatty acids containing 10 to 22, in particular 12 to 18, carbon atoms.

Fatty acids ordinarily contain linear hydrocarbon chains. However, branched chains are also possible in individual cases. The unsaturated fatty acids contain 1 to 3 double bonds, but especially one such bond. As examples of straight chain saturated fatty acids there may be mentioned capric acid, arachinic acid, behenic acid, in particular lauric, myristic, palmitic, margaric and stearic acid; whilst examples of straight chain unsaturated fatty acids are decenoic, undecenoic, dodecenoic, tetradecenoic, elaidic, licosenic acid, especially oleic, linoleic, linolenic and erucic acid. In particular, technical mixtures of the above acids are eligible. As examples of acids with branched chains mentioned may be made of isostearic acid, which, in addition to palmitic and stearic acids, contains α-methylmargaric acid as principal constituent, and isodecyl acid, which consists of a mixture of an isomeric mixture of trimethylheptyl and dimethyloctyl acids as principal constituent. Oleic and stearic acid are preferred.

In the formulae (1.1) and (1.3), the fatty acid radicals are attached to the quaternary nitrogen atom through an amino-alkylene bridge containing 2 or 3 carbon atoms, i.e. an amino-ethylene or an amino-n-propylene bridge. The fatty acid radicals can also be in the form of N-methylolated fatty acid amide radicals and are then attached to the quaternary nitrogen atom through an ether alkylene bridge which contains 2 carbon atoms. In formula (1.2), two fatty acid radicals are attached to an alkylenetriamine containing 4 to 6 carbon atoms, i.e. to diethylenetriamine, di-n-propylenetriamine or N-aminoethyl-N-aminopropylamine.

In addition to representing a radical of the formula (1.3), $R_2$ and $R_3$ also represent alkyl, such as isobutyl, sec-butyl, n-butyl, propyl, isopropyl, preferably ethyl or especially methyl; 2-hydroxy-n-propyl or especially 2-hydroxyethyl, which, although less preferred, can also be etherified by isobutyl, n-butyl, especially ethyl or methyl; or represent 3-cyano-n-propyl, 2-cyanopropyl or especially 2-cyanoethyl.

Finally, $R_2$ and $R_3$ together also represent a heterocyclic ring containing 2 nitrogen atoms which, with the quaternary nitrogen atom, forms a tetrahydropyrimidine ring.

Accordingly, further preferred ammonium salts have the formula

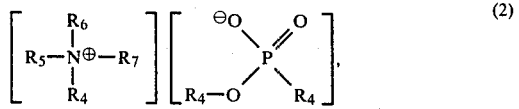  (2)

wherein $R_5$ represents a radical of one of the formula $$A_5-CO-NH-(CH_2-O)_{x_3-1}-(CH_2)_{n_5}- \quad (2.1)$$

or

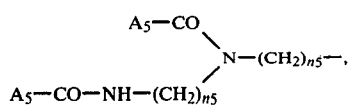

(2.2)

$R_6$ represents ethyl, methyl, 2-hydroxyethyl or a radical of the formula (2.1), $R_7$ represents ethyl, methyl, 2-hydroxyethyl or 2-cyanoethyl, or $R_6$ and $R_7$ together with the quaternary nitrogen atom to which they are attached represent a ring of the formula

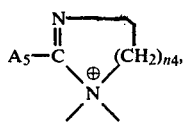

(2.3)

$R_4$ represents ethyl or preferably methyl, $A_5$ represents alkyl or alkenyl of 11 to 17 carbon atoms, $x_3$ is 1 or 2, and each of $n_4$ and $n_5$ is 2 or 3, and especially have one of the formulae

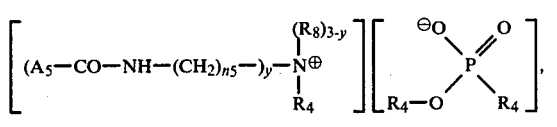

(3)

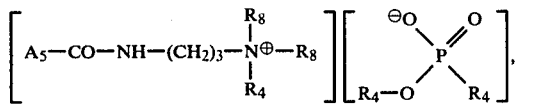

(4)

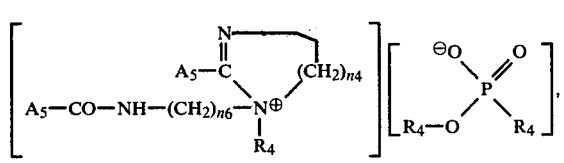

(5)

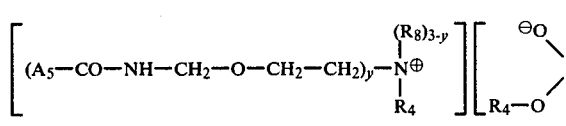

(6)

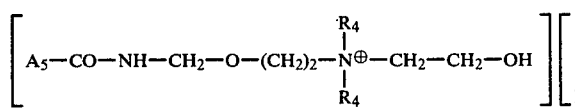

(7)

or

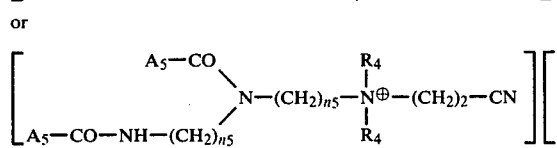

(8)

wherein $R_4$ and $A_5$ have the indicated meanings, $R_8$ represents ethyl, methyl, 2-hydroxyethyl or 2-cyanoethyl, each of $n_4$, $n_5$ and $n_6$ is 2 or 3 and y is 1 or 2.

Specific representatives of the ammonium salts of the formula (3) have for example the formula

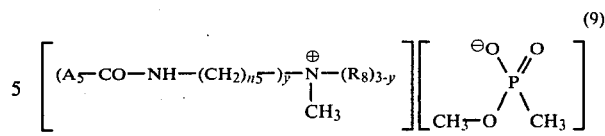

(9)

in which $n_5$, y, $A_5$ and $R_8$ have the following meanings:

| formula no. of the ammonium salt | \multicolumn{4}{c}{meanings of} | | | |
|---|---|---|---|---|
| | $n_5$ | y | $A_5$ | $R_8$ |
| (9.1) | 3 | 1 | —$C_{17}H_{33}$ | —$CH_3$ |
| (9.2) | 3 | 1 | —$C_{17}H_{35}$ | —$CH_3$ |
| (9.3) | 3 | 1 | —$C_{16}H_{31}$ | —$CH_3$ |
| (9.4) | 3 | 1 | —$C_{11}H_{23}$ | —$CH_3$ |
| (9.5) | 3 | 1 | —$C_{17}H_{33}$ | —$CH_2$—$CH_3$ |
| (9.6) | 3 | 1 | —$C_{17}H_{33}$ | —$CH_2$—$CH_2$—OH |
| (9.7) | 2 | 2 | —$C_{17}H_{35}$ | —$CH_2$—$CH_2$—CN |

Specific representatives of the ammonium salts of the formula (5) have for example the formula (10)

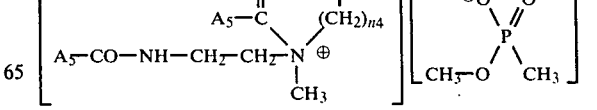

in which $n_4$ and $A_5$ have the following meanings:

| formula no. of the ammonium salt | meanings of | |
|---|---|---|
| | $n_4$ | $A_5$ |
| (10.1) | 2 | $-C_{17}H_{35}$ |
| (10.2) | 2 | $-C_{17}H_{33}$ |
| (10.3) | 2 | $-C_{15}H_{31}$ |
| (10.4) | 2 | $-C_{19}H_{39}$ |
| (10.5) | 2 | $-C_{21}H_{43}$ |
| (10.6) | 3 | $-C_{17}H_{35}$ |
| (10.7) | 3 | $-C_{17}H_{33}$ |
| (10.8) | 3 | $-C_{15}H_{31}$ |
| (10.9) | 3 | $-C_{19}H_{39}$ |
| (10.10) | 3 | $-C_{21}H_{43}$ |

Specific representatives of the ammonium salts of the formula (6) have for example for formula

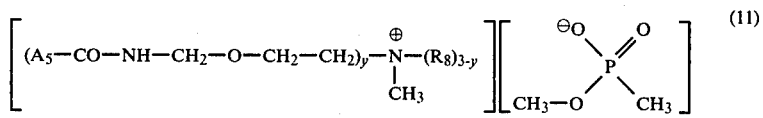

in which y, $A_5$ and $R_9$ have the following meanings:

| formula no. of the ammonium salt | meanings of | | |
|---|---|---|---|
| | y | $A_5$ | $R_8$ |
| (11.1) | 2 | $-C_{17}H_{35}$ | $-CH_2-CH_2-OH$ |
| (11.2) | 2 | $-C_{17}H_{33}$ | $-CH_2-CH_2-OH$ |
| (11.3) | 2 | $-C_{21}H_{43}$ | $-CH_2-CH_2-OH$ |
| (11.4) | 2 | $-C_{19}H_{39}$ | $-CH_2-CH_2-OH$ |
| (11.5) | 2 | $-C_{16}H_{33}$ | $-CH_2-CH_2-OH$ |
| (11.6) | 2 | $-C_{15}H_{31}$ | $-CH_2-CH_2-OH$ |
| (11.7) | 2 | $-C_{14}H_{29}$ | $-CH_2-CH_2-OH$ |
| (11.8) | 2 | $-C_{12}H_{25}$ | $-CH_2-CH_2-OH$ |
| (11.9) | 2 | $-C_{11}H_{23}$ | $-CH_2-CH_2-OH$ |
| (11.10) | 1 | $-C_{17}H_{35}$ | $-CH_2-CH_2-OH$ |
| (11.11) | 1 | $-C_{15}H_{31}$ | $-CH_2-CH_2-OH$ |
| (11.12) | 1 | $-C_{17}H_{35}$ | $-CH_3$ |
| (11.13) | 1 | $-C_{17}H_{35}$ | $-CH_2-CH_3$ |

Specific representatives of the ammonium salts of the formula (8) have for example the formula

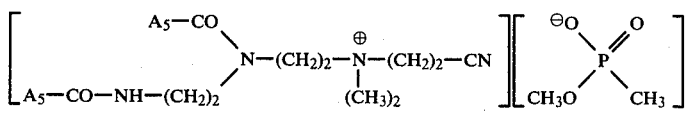

in which $A_5$ has the following meanings:

| formula no. of the ammonium salt | meaning of $A_5$ |
|---|---|
| (12.1) | $-C_{17}H_{35}$ |
| (12.2) | $-C_{17}H_{33}$ |
| (12.3) | $-C_{17}H_{29}$ |
| (12.4) | $-C_{15}H_{31}$ |
| (12.5) | $-C_{11}H_{23}$ |

Preferred ammonium salts are in particular those of one of the formulae (9.7), (10.3), (11.1), (11.6), (11.10), (11.11), (12.1), (12.4), and especially the ammonium salt of one of the formulae (9.1) or (10.1).

The ammonium salts of the formula (1) are obtained in a manner which is in itself known by reacting together a compound which contains at least one fatty acid radical and a quaternisable basic nitrogen atom, i.e. a tertiary amine of the formula

wherein $R_1$, $R_2$ and $R_3$ have the indicated meanings, and a dialkyl ester of an alkylphosphonic acid of the formula

wherein $R_4$ has the indicated meaning.

Preferably, the reaction is carried out in the melt or in a solvent at 60° to 140° C., in particular at 80° to 120° C. Suitable inert solvents for the reaction include optionally halogenated aromatic hydrocarbons, for example benzene, toluene, xylene, chlorobenzene, cycloaliphatic or heterocyclic hydrocarbons, for example dioxane or tetrahydrofurane, optionally halogenated aliphatic hydrocarbons, for example hexane, heptane, octane or the mixtures thereof that occur in petroleum distillate, trichloro- and tetrachloroethylene, aliphatic ethers, for example dimethoxy diethylene glycol, or aliphatic amides, for example dimethyl formamide.

When concurrently using such inert solvents, the reaction is advantageously carried out at the reflux temperature of the solvent employed. Most advantageously, however, the reaction is carried out in the melt at temperatures from 110° to 120° C.

The reaction is ordinarily carried out with equimolar amounts of the starting materials of the formula (13) and (14) or preferably with a slight excess of about 5 to 10 percent, based on the molar amounts, of phosphonic acid derivatives of the formula (14).

The starting materials of the formulae (13) and (14) are known. In particular, the tertiary amines are described as starting materials for the production of the ammonium salts of the formulae (3), (4), (9) and (9.1) to (9.7) in British patent specifications 966,822 and 971,527, as starting materials for the production of the ammonium salts of the formulae (5), (10) and (10.1) to (10.10) in British patent specification No. 1,453,296, as starting materials for the production of the ammonium salts of the formulae (6), (7), (11), and (11.1) to (11.13) in British patent specifications Nos. 600,707 and 782,974, and as starting materials for the production of the ammonium salts of the formulae (8), (12) and (12.1) to (12.5) in British patent specification No. 773,336.

The ammonium salts of the present invention are used in particular as antistatic agents and softening agents in the paper and textile industries.

If the radicals $A_1$ to $A_4$ in the formulae (1.1) to (1.4) represent higher fatty acid radicals containing 15 to 21, preferably 15 to 17, carbon atoms, the softening properties predominate over the antistatic properties. On the other hand, if the radicals $A_1$ to $A_4$ represent lower fatty acid radicals containing preferably 11 to 13 carbon atoms, the softening properties are of lubricant character. If the radicals $A_1$ to $A_4$ represent fatty acid radicals with threefold, twofold and simple unsaturation and containing 10 to 21 carbon atoms, preferably with simple unsaturation and containing 17 carbon atoms, then the antistatic properties are predominant and the ammonium salts are then usually in the form of liquid salts.

In addition to the process for the production of the ammonium salts of the present invention and the use thereof as softening agents and/or antistatic agents, the process for applying the ammonium salts, the composition for carrying out this process, and the substrates treated by this process also constitute further objects of the invention.

The process for finishing organic fibrous material comprises treating said material with a preparation which contains at least one ammonium salt of the invention.

The organic fibrous material which can be finished in accordance with the invention is synthetic or natural material, especially woollen or, most particularly, cellulosic material.

Suitable organic fibrous material comprises in particular papers of any kind, for example coloured or uncoloured papers and cardboards made from bleached or unbleached sulphite or sulphate cellulose. Wallpapers are especially suitable for finishing by the process of the present invention.

The organic fibrous material finished in accordance with the invention can also be dyed or undyed textile fabric in any stage of processing, such as yarns or finished garments, preferably however piece goods, such as wovens, knitted fabrics and fleeces.

The synthetic fibres are for example polyacrylonitrile, in particular polyamide and polyester, fibres. The cellulose component of cellulosic fibres is, inter alia, sisal, ramie, linen and, in particular, cotton. Regenerated cellulose, such as rayon and staple fibres, can also be finished according to the invention. Fibre blends of synthetic and cellulosic fabrics, for example blends of polyester and cotton, polyester and wool or polyamide and wool, are also suitable. Cotton fabrics are particularly suitable for finishing by the process of the invention.

The preparations which are used for carrying out the process of the invention for finishing fibrous materials are preferably in the form of aqueous solutions. Although less preferred, the preparations can also be in the form of solutions in organic solvents, in which case the inert solvents referred to in connection with the production of the ammonium salts of the invention are suitable. In addition, water-soluble lower alcohols and glycols, such as methanol, ethanol or ethylene glycol, are also suitable.

Aside from containing one or more ammonium salts of the invention, the preparation can also contain the ingredients conventionally employed in the paper and textile industries, provided these ingredients are not corrosive. Thus the preparations can contain for example the commercially available fillers, retention agents for fillers, and sequestering agents used in the paper industry, or for example the commercially available wetting agents, buffer substances, and stabilisers employed in the textile industry.

The preparations are applied in the process of the invention to the materials to be finished by known methods, for example by impregnating.

In the paper industry, the ammonium salts are added to the pulp or especially to the surface of paper webs. These latter are sprayed or treated by the immersion method or preferably padded and squeezed out.

In the textile industry, the ammonium salts are applied by the exhaustion process or especially by the padding process to the textile fabrics.

Advantageously 0.2 to 5%, preferably 0.5 to 2% of an approximately 20% by weight solution (±2%) of the ammonium salts of the invention, based on the weight of the fibrous materials to be finished, are used. The amount of ammonium salts applied to the finished fibrous materials is usually 0.1 to 1% by weight, preferably 0.2 to 0.6% by weight.

The fibrous materials impregnated with the ammonium salts are dried. When finished paper, the impregnated paper is dried as a rule at 60° to 120° C. for 60 to 2 minutes. When finishing textiles, the impregnated textile fabric is dried as a rule at 60° to 200° C. for 60 minutes to 20 seconds.

If the ammonium salts are applied by the exhaustion process to the textile fabrics, the process is preferably carried out at 30° to 60° C. for 30 to 10 minutes.

The fibrous materials finished by the process of the invention exhibit excellent antistatic and/or softening effects with a low add-on of ammonium salts. The dry soiling and the fastness to rubbing of the dyeings on dyed fibrous materials are not detrimentally affected, but often even improved. The same also applies to the hydrophilic properties of cellulosic fibres. When dyeing with disperse dyes, an inhibition of migration can also be observed. However, the intrinsic advantage of the present invention resides especially in the fact that the fibrous materials treated with the ammonium salts of the invention do not show any tendency to rust when in contact with iron-containing materials, in contradistinction to materials finished with known antistatic agents and softening agents. This intrinsic advantage is most evident especially when securing wallpapers or furnishing materials with, for example, nails or clips, inter alia in the furniture industry.

The invention is illustrated by the following Examples, in which the parts and percentages are by weight.

MANUFACTURING EXAMPLES

Example 1

90 Parts (0.66 mole) of a 96% dimethyl ester of methylphosphonic acid are added to 243.5 parts of the tertiary amine of the formula

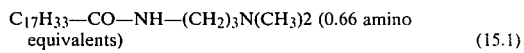
$C_{17}H_{33}$—CO—NH—$(CH_2)_3N(CH_3)_2$ (0.66 amino equivalents)     (15.1)

in the course of 20 minutes at 110° to 120° C.

The reaction mixture is kept for 2 hours at 100°–120° C. and then cooled to 20° C. Yield: 331.7 parts of a water-soluble viscous ammonium salt of the formula (9.1).

Example 2

136 Parts (1.05 moles) of a 96% dimethyl ester of methylphosphonic acid and 684 parts (1 mole) of the tertiary amine of the formula $$(C_{17}H_{35}-CO-NH-CH_2-CH_2)_2NCH_2-CH_2-CN \qquad (15.2)$$

are heated to 110°–115° C. and the reaction mixture is kept for 6 hours at this temperature, then cooled to 20° C. Yield: 816 parts of a solid, water-soluble, wax-like ammonium salt of the formula (9.7). The ammonium salts of the formulae (9.2) to (9.6) are prepared in analogous manner by replacing 1 mole of the tertiary amine of the formula (15.2) by 1 mole of the corresponding tertiary amine.

Example 3

The procedure of Example 2 is repeated using 590 parts (1 mole) of the tertiary amine of the formula $$\begin{array}{c} N \rule{1em}{0.4pt} CH_2 \\ \| \quad \quad | \\ R-C \quad \quad CH_2 \\ \diagdown \diagup \\ N \\ | \\ CH_2-CH_2-NH-CO-R \end{array} \qquad \begin{array}{l} R: 50\% - C_{15}H_{31} \\ 50\% - C_{17}H_{35} \end{array} \qquad (15.3)$$

instead of 1 mole of the tertiary amine of the formula (15.2).

Yield: 720 parts of a solid, water-soluble, wax-like ammonium salt which consists of 50% of the ammonium salt of the formula (10.1) and 50% of the ammonium salt of the formula (10.3).

The ammonium salts of the formulae (10.2) and (10.4) to (10.10) are prepared in analogous manner by replacing 1 mole of the tertiary amine of the formula (15.3) by 1 mole of the corresponding tertiary amine.

Example 4

The procedure of Example 2 is repeated using 431 parts (1 mole) of the tertiary amine of the formula $$R-CO-NH-CH_2-O-CH_2-CH_2N(CH_2-CH_2-OH)_2 \qquad (15.4)$$

$$R: 50\% - C_{15}H_{31}$$
$$50\% - C_{17}H_{35}$$

instead of 1 mole of the tertiary amine of the formula (15.2).

Yield: 562 parts of a solid, water-soluble, wax-like ammonium salt which consists of 50% of the ammonium salt of the formula (11.10) and 50% of the ammonium salt of the formula (11.11). The ammonium salts of the formulae (11.12) and (11.13) are prepared in analogous manner by replacing 1 mole of the tertiary amine of the formula (15.4) by 1 mole of the corresponding tertiary amine.

Example 5

The procedure of Example 2 is repeated using 712 parts (1 mole) of the tertiary amine of the formula $$(R-CO-NH-CH_2-O-CH_2-CH_2)_2NCH_2-CH_2-OH \qquad (15.5)$$

$$R: 50\% - C_{15}H_{31}$$
$$50\% - C_{17}H_{35}$$

instead of 1 mole of the tertiary amine of the formula (15.2).

Yield: 844 parts of a solid, water-soluble, wax-like ammonium salt which consists of 50% of the ammonium salt of the formula (11.1) and 50% of the ammonium salt of the formula (11.6).

The ammonium salts of the formulae (11.2) to (11.5) and (11.7) to (11.9) are prepared in analogous manner by replacing 1 mole of the tertiary amine of the formula (15.5) by 1 mole of the corresponding tertiary amine.

Example 6

The procedure of Example 2 is repeated using 699 parts (1 mole) of the tertiary amine of the formula $$\begin{array}{c} C_{17}H_{35}-CO \diagdown \quad \quad \quad \diagup CH_3 \\ N-CH_2-CH_2-N \\ \diagup \quad \quad \quad \diagdown \\ C_{17}H_{35}-CO-NH-CH_2-CH_2 \quad \quad CH_2-CH_2-CN \end{array} \qquad (15.6)$$

instead of 1 mole of the tertiary amine of the formula (15.2).

Yield: 831 parts of a solid, wax-like ammonium salt of the formula (12.1) which is soluble in hot water. The ammonium salts of the formulae (12.2) to (12.5) are prepared in analogous manner by replacing 1 mole of the tertiary amine of the formula (15.6) by 1 mole of the corresponding tertiary amine.

APPLICATION EXAMPLES

Polyester and polyamide fabric are padded with an aqueous liquor which contains 6 g/l of the ammonium salt of the formula (9.1). The liquor pick-up is 80%. Then one part of the padded fabric is subjected to a heat treatment of 130° C. for 30 seconds, i.e. to a thermofixation, and another part is subjected to a heat treatment of 200° C. for 30 seconds, i.e. to a thermosol process. The resulting antistatic effects obtained are reported on Table 1.

TABLE 1

| Type of fabric | | Temperature of the heat treatment over 30 secs | Surface resistance in $\Omega/cm^2$ |
| --- | --- | --- | --- |
| polyester | untreated | 130° C. | $4 \cdot 10^{14}$ |
|  |  | 200° C. | $1 \cdot 10^{14}$ |
|  | treated | 130° C. | $1 \cdot 10^9$ |
|  |  | 200° C. | $6 \cdot 10^8$ |
| polyamide | untreated | 130° C. | $2 \cdot 10^{13}$ |
|  |  | 200° C. | $2,5 \cdot 10^{12}$ |
|  | treated | 130° C. | $5 \cdot 10^8$ |
|  |  | 200° C. | $5 \cdot 10^8$ |

Similar results are obtained with the ammonium salts of one of the formulae (9.3) to (9.6).

Example 8

Oxygen is introduced for 14 hours through a column chromatography tube which contains steel filings covered with a layer of a 4% solution of the ammonium salt of the formula (9.1). The rust formation is assessed by determining the increase in weight of the column chromatography tube after 14 hours. This test is repeated with a 4% solution of the adduct of the tertiary amine of the formula (15.1) and dimethyl sulphate. This product has the formula

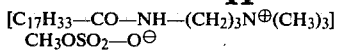
$$CH_3OSO_2-O^\ominus \quad (16)$$

The increase in weight on using the quaternary methyl sulfphate of the formula (16) is 11.7%, but is only 2.5% on using the ammonium salt of the formula (9.1). Similar results are obtained with the ammonium salts of one of the formulae (9.2) to (9.7), (10.1) to (10.10), (11.1) to (11.13) and (12.1) to (12.5).

Example 9

A viscose fabric and a polyacrylic fabric are treated for 20 minutes at 40° C. and pH 4 with 0.1%, based on the weight of the fabric, of the ammonium salt of the formula (10.1) by the exhaustion process. The soft handle effect is evaluated by a rating from 0 to 4, in which 0 denotes no influence on the handle and 4 denotes a very good soft handle. The untreated fabrics have a zero rating, whereas the treating viscose fabric and polyester fabric each have a rating of 3.5.

Similar results are obtained with the ammonium salts of the formulae (9.2), (9.7), (10.5), (10.6), (10.9), (10.10), (11.1), (11.3) to (11.6), (11.10) to (11.13), (12.1) and (12.4).

Example 10

A polyester/wool fabric (1:1) is treated on a padder with 8 g/l of a quaternary substance of Example 1. The liquor pick-up is 100%. The finished fabric can be processed during confectioning without the normally occurring electrostatic charge.

Synthetic fibrous materials of polyamide, polyester, polyacrylonitrile, modified polyacrylonitrile, cellulose acetate, cellulose triacetate and mixtures thereof with wool, cotton and viscose staple fibre exhibit analogous antistatic effects. The product of Example 1 is employed in such an amount as to correspond to applications of 0.04 to 0.24%.

Example 11

Freshly prepared sized galley-proof paper containing 30% of wood pulp, 25% of bleached sulphite cellulose, 25% of waste paper, 20% of bleached sulphate cellulose, as well as the additives China clay, talc and alaun, exits from a drying oven at a speed of 120 m/minute and 40 kg of paper per minute. This paper web is sprayed with a 5% aqueous solution of the product of Example 1, such that 30 g or 60 g of substance per 100 kg of paper are applied, corresponding to an add-on of 0.3 or 0.6% respectively.

During printing, the treated paper runs very well through the printing machine, whereas the untreated paper runs poorly on account of static charge.

Surface resistance measured:
30 g of product of Example 1 per 100 kg of paper: $4.1 \cdot 10^{10} \Omega$
60 g of product of Example 1 per 100 kg of paper: $2.7 \cdot 10^{10} \Omega$

What is claimed is:

1. An ammonium salt of the formula

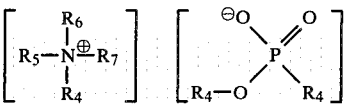

in which
$R_5$ is a radical of the formulae $$A_5-CO-NH-(CH_2-O)_{x_3-1}-(CH_2)_{n_5}-$$

or

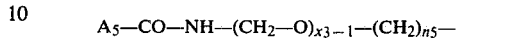

$R_6$ is ethyl, methyl, 2-hydroxyethyl or a radical of the formula $$A_5-CO-NH-(CH_2-O)_{x_3}-CH_2)_{n_5}-,$$

$R_7$ is ethyl, methyl, 2-hydroxyethyl or 2-cyanoethyl, $R_4$ is ethyl or methyl, $A_5$ is alkyl or alkenyl of 11 to 17 carbon atoms, $x_3$ is 1 or 2 and $n_5$ are 2 or 3.

2. An ammonium salt according to claim 1 of the formula

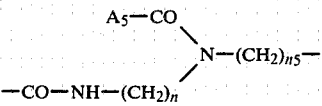

in which $R_4$ is ethyl or methyl, $R_8$ is ethyl, methyl, 2-hydroxyethyl or 2-cyanoethyl, $A_5$ is alkyl or alkenyl of 11 to 17 carbon atoms, $n_5$ is 2 or 3 and $y$ is 1 or 2.

3. An ammonium salt according to claim 1 of the formula

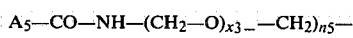

in which $R_4$ is ethyl or methyl, $R_8$ is ethyl, methyl, 2-hydroxyethyl or 2-cyanoethyl, and $A_5$ is alkyl or alkenyl of 11 to 17 carbon atoms.

4. An ammonium salt according to claim 1 of the formula

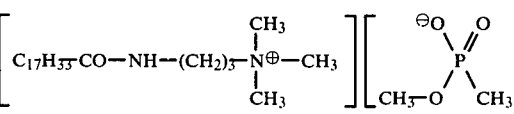

5. An ammonium salt according to claim 1 of the formula

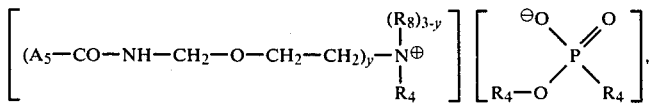

in which $R_4$ is ethyl or methyl, $R_8$ is ethyl, methyl, 2-hydroxyethyl or 2-cyanoethyl, $A_5$ is alkyl or alkenyl of 11 to 17 carbon atoms and y is 1 or 2.

6. An ammonium salt according to claim 1 of the formula

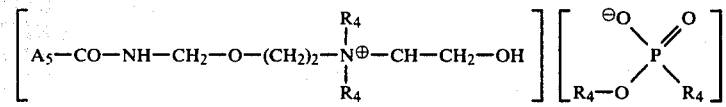

in which $R_4$ is ethyl or methyl and $A_5$ is alkyl or alkenyl of 11 to 17 carbon atoms.

7. An ammonium salt according to claim 1 of the formula

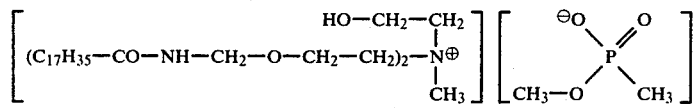

8. An ammonium salt according to claim 1 of the formula

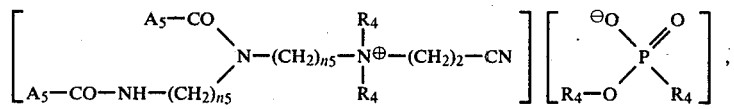

in which $R_4$ is ethyl or methyl, $A_5$ is alkyl or alkenyl of 11 to 17 carbon atoms and $n_5$ is 2 or 3.

9. An ammonium salt according to claim 1 of the formula

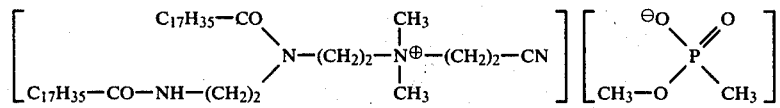

* * * * *